United States Patent
Lu et al.

(10) Patent No.: US 10,973,807 B2
(45) Date of Patent: *Apr. 13, 2021

(54) PHARMACEUTICAL COMPOSITION COMPRISING PYRROLO-FUSED SIX-MEMBERED HETEROCYCLIC COMPOUND

(71) Applicant: Jiangsu Hengrui Medicine Co., Ltd., Jiangsu (CN)

(72) Inventors: Yun Lu, Jiangsu (CN); Xinhua Zhang, Jiangsu (CN); Chenyang Wang, Jiangsu (CN); Tonghui Liu, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 19 days.

This patent is subject to a terminal disclaimer.

(21) Appl. No.: 16/079,589

(22) PCT Filed: Feb. 28, 2017

(86) PCT No.: PCT/CN2017/075111
§ 371 (c)(1),
(2) Date: Aug. 24, 2018

(87) PCT Pub. No.: WO2017/148359
PCT Pub. Date: Sep. 8, 2017

(65) Prior Publication Data
US 2019/0054073 A1   Feb. 21, 2019

(30) Foreign Application Priority Data
Mar. 1, 2016 (CN) .......................... 201610116472.2

(51) Int. Cl.
*A61K 31/437* (2006.01)
*A61K 9/16* (2006.01)
*A61K 9/48* (2006.01)

(52) U.S. Cl.
CPC .......... *A61K 31/437* (2013.01); *A61K 9/1623* (2013.01); *A61K 9/4858* (2013.01)

(58) Field of Classification Search
CPC ..... A61K 31/437; A61K 9/4858; A61K 47/26
See application file for complete search history.

(56) References Cited

U.S. PATENT DOCUMENTS

2010/0004239 A1* 1/2010 Tang .................... C07D 471/04
514/234.5
2013/0338131 A1* 12/2013 Staric .................. A61K 9/2018
514/210.02

FOREIGN PATENT DOCUMENTS

| CN | 101007814 A | 8/2007 |
| CN | 102266300 A | 12/2011 |
| WO | 2007085188 A1 | 8/2007 |

OTHER PUBLICATIONS

Sandler Expert Opinion Drug Review p. 228 (Year: 2011).*
The second method of general rule 0931 of vol. IV of Chinese Pharmacopoeia 2015 Edition.
Int'l Search Report dated Jun. 1, 2017 in Int'l Application No. PCT/CN2017/07511.
Liu et al, "Clinical Efficacy of Famitinib Malate for Treatment of Metastatic Renal Cell Carcinoma—a Report of 9 Case," Academic Journal of Second Military Medical University, vol. 36, No. 12, pp. 1348-1351 (Dec. 2015).

* cited by examiner

*Primary Examiner* — Matthew P Coughlin
*Assistant Examiner* — Thurman Wheeler
(74) *Attorney, Agent, or Firm* — Ice Miller LLP

(57) ABSTRACT

The present invention provides a pharmaceutical composition containing a pyrrolo-fused six-membered heterocyclic compound or a pharmaceutically acceptable salt of the compound. Specifically, the invention provides a pharmaceutical composition containing 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof, and at least one water soluble filler. The pharmaceutical composition of the invention features a rapid dissolution and good stability.

10 Claims, 1 Drawing Sheet

PHARMACEUTICAL COMPOSITION COMPRISING PYRROLO-FUSED SIX-MEMBERED HETEROCYCLIC COMPOUND

CROSS-REFERENCE TO RELATED APPLICATIONS

This application is a Section 371 of International Application No. PCT/CN2017/075111, filed Feb. 28, 2017, which was published in the Chinese language on Sep. 8, 2017, under International Publication No. WO 2017/148359 A1, which claims priority under 35 U.S.C. § 119(b) to Chinese Application No. 201610116472.2, filed Mar. 1, 2016, the disclosures of which are incorporated herein by reference in their entirety.

FIELD OF THE INVENTION

The present invention belongs to the field of pharmaceutical formulations. Specifically, the present invention relates to a pharmaceutical composition comprising 5-(2-diethyl-amino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof.

BACKGROUND OF THE INVENTION

With the development of molecular biology technology and further understanding of the pathogenesis of tumors from the molecular level of cellular receptors and proliferation regulation, the therapy targeting cell receptors, key genes, and regulatory molecules begins to enter the clinic, which is called as "molecular targeted therapy." These fields include targeted epidermal growth factor receptor (EGFR) blockers, monoclonal antibodies targeting certain specific cell markers, drugs targeting certain oncogenes and cytogenetic markers of cancers, anti-tumor angiogenesis drugs, anti-tumor vaccines, and gene therapies etc.

The antitumor mechanism of tyrosine kinase inhibitors (TKIs) that first entered the clinic can be achieved by the following ways: inhibiting injury repair of tumor cells, blocking cell division in the G1 phase, inducing and maintaining cell apoptosis, and anti-neovascularization, etc. Overexpression of EGFR often indicates poor prognosis, rapid metastasis, resistance to chemotherapeutic drugs, resistance to hormones, and shorter life span, etc., in patients. TKIs can also inhibit the "cross-talk" between the two signaling transduction pathways of EGFR and vascular endothelial growth factor receptor (VEGFR) by down-regulating the angiogenic factor in tumor cells and inhibiting the signaling transduction of EGFR on tumor vascular endothelial cells. It provides a reasonable basis for clinical inhibition of both transduction pathways simultaneously. Results of clinical trials show that multi-target inhibitors are superior to single-target inhibitors in terms of treatment. Multi-targets in combination with blocking of signaling transduction is a new direction for tumor therapy and drug development.

Up to now, the FDA has approved multiple multi-target TKIs, such as sorafenib, vandetanib, and Sunitinib (Sutent, SU-11248). Among them, Sunitinib was approved in January 2006 for treating GIST and advanced kidney cancer. Since there are currently no drugs for the treatment of advanced GIST in the clinic except for imatinib, and there are few drugs for kidney cancer, the results of Sunitinib are encouraging. WO2007085188 discloses a compound similar to Sunitinib, as shown in formula (I) below, which can be better applied to the treatment of the above tumors. The chemical name of the compound is 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one. It is known to inhibit tumor proliferation and angiogenesis, and selectively inhibit the kinase activity of vascular endothelial growth factor (VEGF) receptor. It can be used clinically for the treatment of various tumors such as kidney cancer, gastrointestinal stromal tumor, colorectal cancer, and pancreatic neuroendocrine tumor, etc.

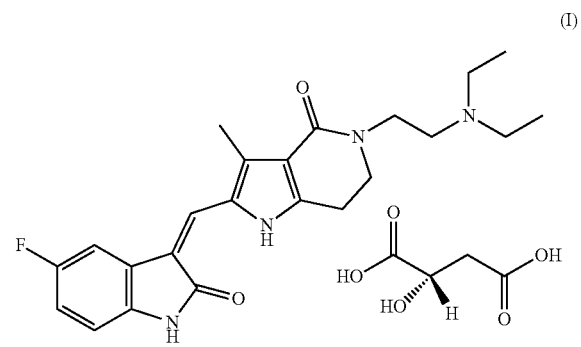

(I)

Since the compound of formula (I) or a pharmaceutically acceptable salt thereof has a poor water solubility, and is unstable in the presence of moisture, when the compound of formula (I) or a pharmaceutically acceptable salt thereof is formulated into a pharmaceutical composition by using a conventional pharmaceutical excipient, the resulting composition is difficult to dissolve rapidly and keep its quality stable.

BRIEF SUMMARY OF THE INVENTION

The object of the present invention is to provide a pharmaceutical composition with a good stability and rapid dissolution. The process for preparing the pharmaceutical composition is simple and is more suitable for large-scale production.

The pharmaceutical composition according to the present invention comprises an active ingredient and at least one water-soluble filler. The active ingredient is 5-(2-diethyl-amino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof.

The water-soluble filler can be a sugar alcohol, preferably one or more of lactose, glucose, sucrose, mannitol, and sorbitol.

In a preferred embodiment of the present invention, the water-soluble filler is mannitol.

The above water-soluble filler can promote the dissolution of the active ingredient and keep its stability. The content of the water-soluble filler of the present invention is not particularly limited. In a preferred embodiment of the present invention, the water-soluble filler can be present in an amount of 20%-95%, preferably 30%-90%, more preferably 40%-85%, and most preferably 50%-80% by weight, relative to the total weight of the composition.

In the pharmaceutical composition of the present invention, the pharmaceutically acceptable salt of the active ingredient can be selected from the group consisting of hydrochloride, malate, hydrobromide, p-toluenesulfonate, methanesulfonate, sulfate, and ethanesulfonate, preferably malate. The active ingredient can be present in an amount of 3%-40%, preferably 5%-30%, and most preferably 10%-20% by weight, relative to the total weight of the composition.

The pharmaceutical composition according to the present invention can comprise at least one other filler, for example one or more of starch, pregelatinized starch, dextrin, and microcrystalline cellulose, etc. The at least one other filler is present in an amount of about 5%-50% by weight, relative to the total weight of the composition.

The pharmaceutical composition according to the present invention can comprise a disintegrant, wherein the disintegrant is one or more selected from the group consisting of croscarmellose sodium, sodium carboxymethyl starch, low substituted hydroxypropyl cellulose and crospovidone. The disintegrant is preferably present in an amount of about 1%-20% by weight, relative to the total weight of the composition.

The pharmaceutical composition according to the present invention can further comprise one or more lubricant(s) that facilitates capsule filling or tableting. The lubricant can be selected from the group consisting of talc, magnesium stearate, sodium stearyl fumarate, zinc stearate, glyceryl behenate, sodium lauryl sulfate, hydrogenated vegetable oil, and colloidal silicon dioxide, etc. The lubricant is preferably present in an amount of about 0.5%-5% by weight, relative to the total weight of the composition.

The present invention also provides a pharmaceutical composition, comprising or consisting of the following ingredients:
1) 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof, wherein the particle size distribution range d(0.9) thereof is preferably less than 60 μm, and most preferably less than 40 μm;
2) 30-80 wt % of lactose or mannitol;
3) optionally 5-50 wt % of pregelatinized starch;
4) 1-30 wt % of a disintegrant, wherein the disintegrant is one or more selected from the group consisting of croscarmellose sodium, sodium carboxymethyl starch, low substituted hydroxypropyl cellulose and crospovidone; and
5) 0.5-5 wt % of a lubricant, wherein the lubricant is one or more selected from the group consisting of magnesium stearate, sodium stearyl fumarate, colloidal silicon dioxide, and talc.

The pharmaceutical composition of the present invention can be prepared by a conventional method in the art. The active ingredient and water-soluble filler are mixed together and granulated. The granules of the pharmaceutical composition can be prepared by a method such as high shear wet granulation, dry granulation, and wet one step granulation, etc. The granules are then filled into capsules to prepare hard capsules, or compressed into tablets. In the present invention, the granules of the composition are preferably prepared by dry granulation, and are preferably prepared into hard capsules.

When the particle size distribution of the active ingredient of the pharmaceutical composition of the present invention meets a certain requirement, it can promote a more rapid dissolution of the composition. The particle size of the active ingredient is determined by a laser particle size analyzer. d(0.9) should be less than 100 μm, preferably less than 80 μm, more preferably less than 60 μm, and most preferably less than 40 μm.

In the pharmaceutical composition of the present invention, the drug dissolution rate is good due to the presence of the water-soluble filler. The dissolution rate is determined according to the second method of general rule 0931 of volume IV of Chinese Pharmacopoeia 2015 Edition, using purified water (preferably 900 ml) as a dissolution medium at 37±0.5° C. and at a paddle speed of 50 rpm. The dissolution rate is greater than or equal to 80% in 45 minutes.

On the other hand, the pharmaceutical composition of the present invention has a good stability. The degradation product is less than or equal to 0.5% after the composition has been placed at a temperature of 25° C. and relative humidity of 75% for 10 days, or the degradation product is less than or equal to 1% after the composition has been placed at a temperature of 25° C. and relative humidity 90% for 10 days.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
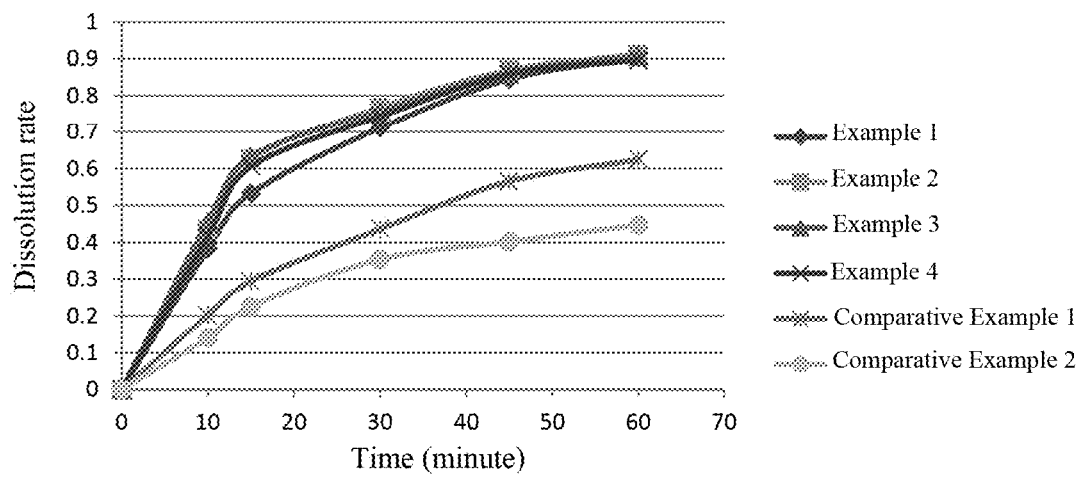
FIG. 1 shows the dissolution profiles of the capsules of Examples 1 to 4 and Comparative Examples 1 and 2 in purified water.

The present invention is further described in detail by the following examples and experimental examples. These examples and experimental examples are for illustrative purposes only, and are not intended to limit the scope of the present invention.

Examples 1-4, Comparative Examples 1-2

5-(2-Diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one malate (hereinafter referred to as compound A), pregelatinized starch, lactose, crospovidone, and silicon dioxide were mixed well according to the prescription ratios of Examples 1-4 shown in Table 1. Dry granulation was carried out by a dry granulator, and a prescription amount of magnesium stearate was then added and mixed well with the granules. The resulting total mixed granules were filled into capsules to prepare the capsules.

Compound A, microcrystalline cellulose, crospovidone, and silicon dioxide were mixed well with calcium hydrophosphate or pregelatinized starch according to the prescription ratios of Comparative Examples 1 and 2 shown in Table 1. Dry granulation was carried out by a dry granulator, and a prescription amount of magnesium stearate was then added and mixed well with the granules. The resulting total mixed granules were filled into capsules to prepare the capsules.

TABLE 1

| Ingredients | Example 1 | Example 2 | Example 3 | Example 4 | Comparative Example 1 | Comparative Example 2 |
|---|---|---|---|---|---|---|
| Compound A | 22.1 | 13.3 | 8.8 | 13.3 | 13.3 | 13.3 |
| Microcrystalline cellulose | 0 | 0 | 0 | 0 | 50.3 | 50.3 |
| Calcium hydrophosphate | 0 | 0 | 0 | 0 | 0 | 30.0 |
| Pregelatinized starch | 33.3 | 15.0 | 0 | 30.0 | 30.3 | 0 |
| Lactose | 38.1 | 67.3 | 86.7 | 50.3 | 0 | 0 |
| Crospovidone | 5.0 | 3.0 | 3.0 | 5.0 | 5.0 | 5.0 |
| Silicon dioxide | 0.5 | 0.5 | 0.5 | 0.5 | 0.5 | 0.5 |
| Magnesium stearate | 1.0 | 1.0 | 1.0 | 1.0 | 1.0 | 1.0 |
| Total | 100 | 100 | 100 | 100 | 100 | 100 |

Unit: weight %

Examples 5-8, Comparative Example 3

Compound A, pregelatinized starch, mannitol, crospovidone, and silicon dioxide were mixed well according to the prescription ratios of Examples 5-8 shown in Table 2. Dry granulation was carried out by a dry granulator, and a prescription amount of magnesium stearate was then added and mixed well with the granules. The resulting total mixed granules were filled into capsules to prepare the capsules of Examples 5-8.

Compound A, pregelatinized starch, calcium hydrophosphate, crospovidone, and silicon dioxide were mixed well according to the prescription ratio of Comparative Example 3 shown in Table 2. Dry granulation was carried out by a dry granulator, and a prescription amount of magnesium stearate was then added and mixed well with the granules. The resulting total mixed granules were filled into capsules to prepare the capsules of Comparative Example 3.

TABLE 2

| Components | Example 5 | Example 6 | Example 7 | Example 8 | Comparative Example 3 |
|---|---|---|---|---|---|
| Compound A | 22.1 | 13.3 | 8.8 | 13.3 | 13.3 |
| Calcium hydrophosphate | 0 | 0 | 0 | 0 | 50.3 |
| Pregelatinized starch | 33.3 | 15.0 | 0 | 30.0 | 30.0 |
| Mannitol | 38.1 | 67.3 | 86.7 | 50.3 | 0 |
| Crospovidone | 5.0 | 3.0 | 3.0 | 5.0 | 5.0 |
| Silicon dioxide | 0.5 | 0.5 | 0.5 | 0.5 | 0.5 |
| Magnesium stearate | 1.0 | 1.0 | 1.0 | 1.0 | 1.0 |
| Total | 100 | 100 | 100 | 100 | 100 |

Unit: weight %

Experimental Example 1: Dissolution Test

The dissolution rates of the capsules of Examples 1-8 and Comparative Examples 1-3 were determined according to the dissolution and release test (the second method of general rule 0931 of volume IV of Chinese Pharmacopoeia 2015 Edition). The dissolution test was carried out using 900 ml of purified water as a dissolution medium at 37±0.5° C. and at a paddle speed of 50 rpm. The results show that in the capsules of Examples 1-8 which comprise mannitol or lactose in the formulation, especially to the capsules of Examples 5-8 which comprise mannitol, the dissolution of compound A is rapid; whereas in the capsules of Comparative Examples 1-3 which do not comprise mannitol or lactose, the dissolution of compound A is slow and incomplete.

Figure 2:
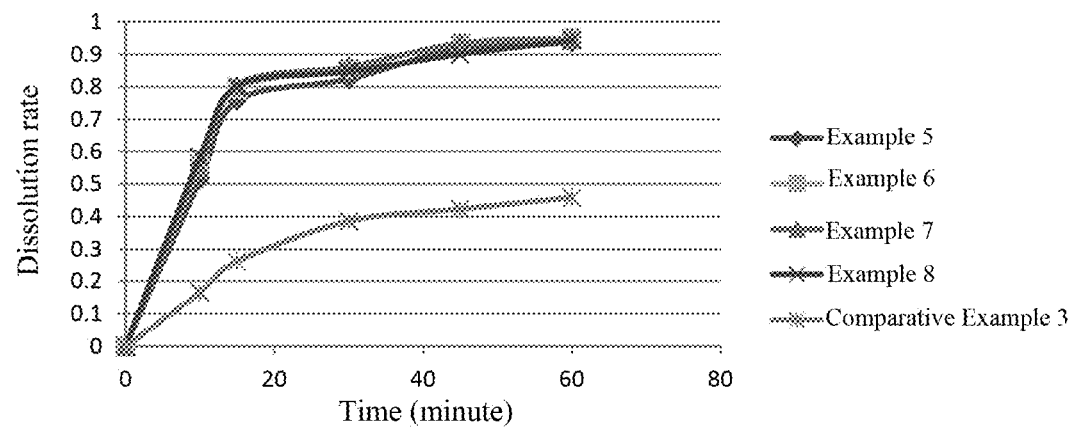
FIG. 2 shows the dissolution profiles of the capsules of Examples 5 to 8 and Comparative Example 3 in purified water.

The dissolution profiles are shown in FIGS. 1 and 2.

Examples 9-11, Comparative Example 4

Compound A of Examples 9-11 and Comparative Example 4 with different particle sizes shown in Table 3, respectively, were mixed well with pregelatinized starch, mannitol, crospovidone, and silicon dioxide according to the prescription ratio of Example 6 shown in Table 2. Dry granulation was carried out by a dry granulator, and a prescription amount of magnesium stearate was then added and mixed well with the granules. The resulting total mixed granules were filled into capsules to prepare the capsules of Examples 9-11 and Comparative Example 4.

TABLE 3

| Samples | Comparative Example 4 | Example 9 | Example 10 | Example 11 |
|---|---|---|---|---|
| Particle size distribution d0.9 of compound A | 128 μm | 67 μm | 55 μm | 37 μm |

Note: The particle size distribution of compound A shown in Table 3 is determined by a Malvern Laser Particle Size Analyzer Mastersizer2000. The refractive index of the particles is 1.520. The injector is Scirocco2000 (A), the analysis mode is universal (fine powder), and the sensitivity is normal.

Experimental Example 2: Dissolution Test

The dissolution rates of the capsules of Examples 9-11 and Comparative Example 4 were determined according to the dissolution and release test (the second method of general rule 0931 of volume IV of Chinese Pharmacopoeia 2015 Edition). The dissolution test was carried out using 900 ml of purified water as a dissolution medium at 37±0.5° C. and at a paddle speed of 50 rpm. The results show that in the capsules of Examples 9-11, as the particle size distribution d0.9 of compound A (with the particle size distribution d0.9 lower than 100 μm) becomes smaller, the dissolution rates of the capsules become gradually faster, indicating that the smaller the particle size distribution d0.9 of compound A, the faster the dissolution rate of the capsules; whereas the particle size of compound A of Comparative Example 4 is more than 100 and the dissolution thereof is slow.

Figure 3:
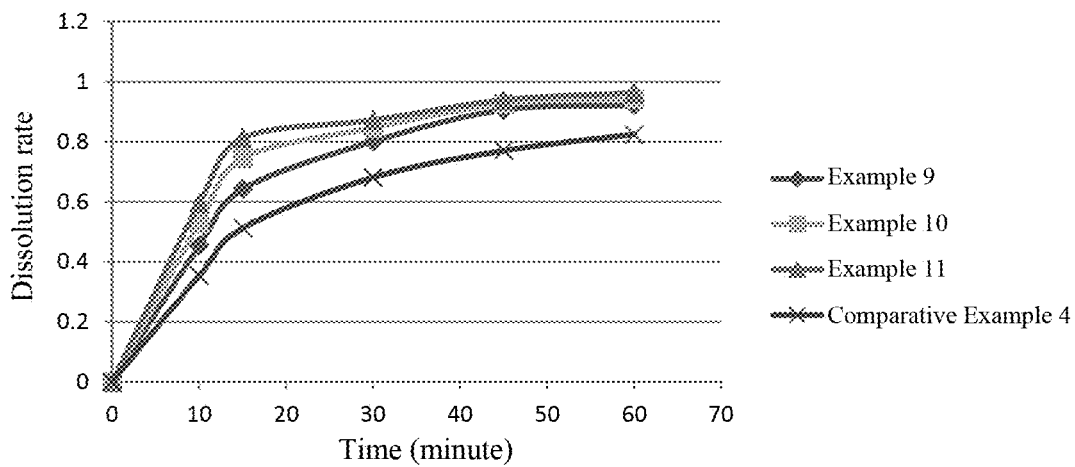
FIG. 3 shows the dissolution profiles of the capsules of Examples 9 to 11 and Comparative Example 4 in purified water.

The dissolution profiles are shown in FIG. 3.

Experimental Example 3: Stability Test

The capsules of Examples 4 and 6, and the capsules of Comparative Examples 1 and 3 were respectively placed under open conditions at a temperature of 25° C. and relative humidity of 75%, or at a temperature of 25° C. and relative humidity of 90% for 5 days and 10 days, and then the degradation products were determined by a HPLC method. The results show that in a high-humidity environment, the growth rates of the degradation products of Examples 4 and 6 which comprise lactose or mannitol are significantly lower than that of Comparative Examples 1 and 3 which do not comprise lactose and mannitol, indicating that the capsules comprising lactose or mannitol are more stable in a high-humidity environment. The results of the test are shown in Table 4.

TABLE 4

| Samples | Degradation product (%) at temperature of 25° C. and relative humidity of 75% | | | Degradation product (%) at temperature of 25° C. and relative humidity of 90% | | |
|---|---|---|---|---|---|---|
| | Initial state | Placed for 5 days | Placed for 10 days | Initial state | Placed for 5 days | Placed for 10 days |
| Example 4 | 0.16 | 0.20 | 0.39 | 0.16 | 0.64 | 0.91 |
| Example 6 | 0.17 | 0.18 | 0.32 | 0.17 | 0.59 | 0.79 |
| Comparative Example 1 | 0.19 | 0.38 | 0.61 | 0.19 | 0.92 | 1.63 |
| Comparative Example 3 | 0.17 | 0.32 | 0.55 | 0.17 | 0.86 | 1.49 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A pharmaceutical composition, comprising:
   1) 10-20 wt % of 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof, having a particle size distribution range d(0.9) thereof less than 60 μm;
   2) 30-80 wt % of lactose or mannitol;
   3) optionally 5-50 wt % of pregelatinized starch;
   4) 1-30 wt % of a disintegrant, wherein the disintegrant is at least one selected from the group consisting of croscarmellose sodium, sodium carboxymethyl starch, low substituted hydroxypropyl cellulose and crospovidone; and
   5) 0.5-5 wt % of a lubricant, wherein the lubricant is at least one selected from the group consisting of magnesium stearate, sodium stearyl fumarate, colloidal silicon dioxide, and talc.

2. The pharmaceutical composition according to claim 1, wherein the composition is a tablet or a capsule.

3. A method of treating cancer, comprising administering to a subject in need thereof the pharmaceutical composition according to claim 1.

4. The method according to claim 3, wherein the cancer is kidney cancer, gastrointestinal stromal tumor, colorectal cancer, or pancreatic neuroendocrine tumor.

5. A method of treating cancer, comprising administering to a subject in need thereof the pharmaceutical composition according to claim 2.

6. The method according to claim 5, wherein the cancer is kidney cancer, gastrointestinal stromal tumor, colorectal cancer, or pancreatic neuroendocrine tumor.

7. A pharmaceutical composition according to claim 1, wherein the composition has a dissolution rate such that at least 80% of the active ingredient is released from the pharmaceutical composition in 45 minutes when measured in a dissolution medium containing water at 37±0.5° C. and at a paddle speed of 50 rpm.

8. A method of treating cancer, comprising administering to a subject in need thereof the pharmaceutical composition according to claim 7.

9. The method according to claim 8, wherein the cancer is kidney cancer, gastrointestinal stromal tumor, colorectal cancer, or pancreatic neuroendocrine tumor.

10. The pharmaceutical composition according to claim 1, wherein the pharmaceutically acceptable salt is selected from the group consisting of hydrochloride, malate, hydrobromide, p-toluenesulfonate, methanesulfonate, sulfate, and ethanesulfonate.

* * * * *